(12) United States Patent
Pouchoulin et al.

(10) Patent No.: US 12,280,190 B2
(45) Date of Patent: Apr. 22, 2025

(54) FLUID WARMING DEVICE FOR AN EXTRACORPOREAL BLOOD TREATMENT APPARATUS AND METHOD FOR DETECTING A FLUID TEMPERATURE AT AN OUTLET OF A FLUID WARMING DEVICE FOR AN EXTRACORPOREAL BLOOD TREATMENT APPARATUS

(71) Applicant: GAMBRO LUNDIA AB, Lund (SE)

(72) Inventors: Dominique Pouchoulin, Tramoyes (FR); Alexander Cain, Minneapolis, MN (US)

(73) Assignee: GAMBRO LUNDIA AB, Lund (SE)

( * ) Notice: Subject to any disclaimer, the term of this patent is extended or adjusted under 35 U.S.C. 154(b) by 698 days.

(21) Appl. No.: 17/283,739

(22) PCT Filed: Oct. 3, 2019

(86) PCT No.: PCT/EP2019/076809
§ 371 (c)(1),
(2) Date: Apr. 8, 2021

(87) PCT Pub. No.: WO2020/074357
PCT Pub. Date: Apr. 16, 2020

(65) Prior Publication Data
US 2021/0379257 A1    Dec. 9, 2021

(30) Foreign Application Priority Data
Oct. 10, 2018   (EP) ..................... 18199718

(51) Int. Cl.
*A61M 1/16*   (2006.01)
*A61M 1/36*   (2006.01)

(52) U.S. Cl.
CPC ...... *A61M 1/1664* (2014.02); *A61M 1/36223* (2022.05); *A61M 2205/127* (2013.01);
(Continued)

(58) Field of Classification Search
CPC ............ A61M 1/1664; A61M 1/36226; A61M 5/44; A61M 2205/127; A61M 2205/3368; A61M 2205/3372; A61M 2205/50
See application file for complete search history.

(56) References Cited

U.S. PATENT DOCUMENTS 6,535,689 B2    3/2003  Augustine
7,158,719 B2 *  1/2007  Cassidy ................ F24H 15/128
                                                       392/494
(Continued)

FOREIGN PATENT DOCUMENTS

CN    101060803    10/2004
CN    108204865    6/2018
(Continued)

OTHER PUBLICATIONS

PCT Search Report and Written Opinion for PCT/EP2019/076809 dated Dec. 10, 2019 (13 pages).
(Continued)

*Primary Examiner* — Benjamin M Kurtz
(74) *Attorney, Agent, or Firm* — Mueting Raasch Group

(57) ABSTRACT

A fluid warming device for an extracorporeal blood treatment apparatus, comprises: an outlet temperature sensor (31) operatively active at an outlet (22) of a fluid warming path (23) to detect a measured outlet temperature (To) of a fluid leaving the fluid warming device (18); an electronic control unit (29) operatively connected to the outlet temperature sensor (31). The electronic control unit (29) is configured to perform the following procedure: receiving, from the outlet temperature sensor (31) a signal correlated to a measured outlet temperature (To); correcting the measured outlet temperature (To) through a correction model to obtain an actual fluid outlet temperature (Tout); adjusting a heating power (Ph) of heating elements to keep the actual fluid outlet temperature (Tout) at a set reference temperature value
(Continued)

(Tset). The correction model is an empirical model of a measurement error (E) derived from a plurality of experimental data sets, the measurement error (E) being a difference between the measured outlet temperature (To) and the actual fluid outlet temperature (Tout).

14 Claims, 5 Drawing Sheets

(52) U.S. Cl.
CPC ............... *A61M 2205/3372* (2013.01); *A61M 2205/3653* (2013.01); *A61M 2205/50* (2013.01)

(56) References Cited

U.S. PATENT DOCUMENTS

| | | |
|---|---|---|
| 7,794,141 B2 | 9/2010 | Perry |
| 7,907,835 B2 | 3/2011 | Boussemart |
| 8,515,267 B2 | 8/2013 | Boussemart |
| 10,398,827 B2 | 9/2019 | Pouchoulin |
| 10,716,888 B2 | 7/2020 | Pouchoulin |
| 11,679,192 B2 | 6/2023 | Pouchoulin |
| 2009/0012655 A1 | 1/2009 | Kienman |

FOREIGN PATENT DOCUMENTS

| | | |
|---|---|---|
| EP | 1132101 | 9/2001 |
| EP | 3120883 | 1/2017 |
| EP | 3275473 | 1/2018 |
| EP | 2021048 B1 | 3/2018 |
| JP | 2000-093449 A | 4/2000 |
| JP | 2009-538214 A | 11/2009 |
| JP | 2017-526481 | 9/2017 |
| WO | WO 00/41746 | 7/2000 |

OTHER PUBLICATIONS

Extended European Search Report for Application No. 18199718 dated Apr. 26, 2019 (3 pages).
Office Action issued in Japan for Application No. 2021-517330 dated Aug. 17, 2023 (10 pages). English translation included.
Office Action issued in China for Application No. 201980066272.2 dated Dec. 23, 2021 (35 pages. English translation included.
Hua fu et al., Sensor Technology, Coal Industry Press, pp. 3-13., Jun. 30, 2015.
Japanese Patent Application No. 2021-517330; Office Action issued Jul. 18, 2024, English language translation included; 8 pages.

\* cited by examiner

FLUID WARMING DEVICE FOR AN EXTRACORPOREAL BLOOD TREATMENT APPARATUS AND METHOD FOR DETECTING A FLUID TEMPERATURE AT AN OUTLET OF A FLUID WARMING DEVICE FOR AN EXTRACORPOREAL BLOOD TREATMENT APPARATUS

This application is a U.S. National Stage Application of International Application No. PCT/EP2019/076809 filed Oct. 3, 2019, which was published in English on Apr. 16, 2020 as International Publication No. WO 2020/074357 A1. International Application No. PCT/EP2019/076809 claims priority to European Application No. 18199718.0 filed Oct. 10, 2018.

Fluid warming device for an extracorporeal blood treatment apparatus and method for detecting a fluid temperature at an outlet of a fluid warming device for an extracorporeal blood treatment apparatus.

DESCRIPTION

Field of the Invention

The present invention relates to a fluid warming device for an extracorporeal blood treatment apparatus and to an extracorporeal blood treatment apparatus comprising a fluid warming device or configured to be coupled to a fluid warming device.

The present invention relates to a fluid warming device coupled or configured to be coupled to an extracorporeal blood circuit of the extracorporeal blood treatment apparatus to heat blood (blood warming device) and/or to a fluid warming device coupled or configured to be coupled to a treatment fluid circuit of the extracorporeal blood treatment apparatus to heat treatment fluid (treatment fluid warming device).

The present invention relates to a method for detecting a fluid temperature at an outlet of the fluid warming device.

In particular, the present invention relates to the correction of temperature measurement provided by contact temperature sensors, like thermistors or thermocouples, at the outlet of the fluid warming device.

Extracorporeal blood treatment involves removing blood from a patient, treating the blood externally to the patient, and returning the treated blood to the patient. Extracorporeal blood treatment is typically used to extract undesirable matter or molecules from the patient's blood and add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, or to perform extracorporeal gas exchange processes, for example.

Extracorporeal blood treatment is typically accomplished by removing the blood from the patient in e.g. a continuous flow, introducing the blood into a primary chamber, also referred to as blood chamber, of a treatment unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment.

During extracorporeal blood treatment therapies, the patient may lose significant amount of heat due to fluid exchange by diffusion or convection, and due to heat lost to the atmosphere. As extracorporeal blood treatments may last from several hours up to several days, the patient is put at risk of hypothermia in case no preventive measures are taken. This risk is, for example, present both in the case of relatively short treatments with high volume exchange, like chronic haemodialysis (HD), and in the case of low volume but continuous therapies like continuous renal replacement therapy (CRRT). Furthermore, the risk of hypothermia is even more problematic in case of treatments applied to low body weight patients, such as children. Blood cooling due to fluid exchange (dialysate, infusion or both) or due to water evaporation during gas exchange processes is usually more important than heat losses to atmosphere in the complete extracorporeal blood circuit.

In order to prevent hypothermia during extracorporeal blood treatment, blood warmers acting on the bloodline and capable of directly warming blood and treatment fluid warmers acting on the treatment fluid circuit to heat treatment fluid/s prior to their infusion in the blood circuit or treatment unit have been used.

BACKGROUND

Measurement of the blood/fluid temperature at an outlet of blood/fluid warmer is known and it is used to control the blood/fluid warming device, in order to adjust the temperature of the treated blood returning to the patient and to drive the patient temperature on the long run.

Document U.S. Pat. No. 6,535,689 relates to an intravenous fluid warming system with a removable heat exchanger. The system includes a warming unit for warming the fluid and an inlet slot for receiving a heat exchanger which is embodied as a cassette. An exit temperature of the warmed fluid at an exit port is monitored by a temperature sensor located near a fluid outlet port. The fluid outlet port may have an infrared thermometer, integral heat sensor, or thermocouple for sensing the fluid temperature.

Disadvantages of most of known solutions are related to lack of accuracy of the temperature measurements at the outlet of the blood/fluid warmers, in particular of the measurements performed through contact temperature sensors, like thermistors and thermocouples.

These types of temperature sensor are required to be in physical contact with the object being sensed and use conduction to monitor changes in temperature. In blood/fluid warmers these types of temperature sensor are placed in contact with bag, cassette or tubing in which blood/fluid flows.

SUMMARY OF THE INVENTION

In view of the above, it is an object of embodiments according to the present invention to improve the reliability of the fluid warming devices for extracorporeal blood treatment apparatuses and to improve the reliability of the extracorporeal blood treatment apparatuses employing said fluid warming devices.

It is an object of embodiments according to the present invention to improve controlling the temperature of the treated blood returning to the patient and driving the patient temperature on the long run.

In particular, it is an object to provide a fluid warming device wherein the reliability and accuracy of the fluid temperature measurement at the outlet of the fluid warming device is improved.

It is a further object to provide for optimized fluid temperature accuracy for a given design of a fluid warming device and/or of an extracorporeal blood treatment apparatus.

It is a further object to provide a fluid warming device and/or an extracorporeal blood treatment apparatus with the mentioned improved accuracy which, at the same time, is/are structurally simple, reliable and cost effective.

It is a further object to provide said reliability and accuracy avoiding development of complex and cumbersome insulation of the sensor/s.

It is a further object to provide said reliability and accuracy without impacting costs of the device and/or apparatus.

At least one of the above objects is substantially achieved by correcting a temperature measurement performed by a contact temperature sensor at the outlet of the fluid warming device through an empirical model of a measurement error derived from other available parameters.

In particular, at least one of the above objects is substantially achieved by a fluid warming device and a method for detecting a fluid temperature at an outlet of a fluid warming device according to one or more of the appended claims.

Aspects of the invention are disclosed in the following.

In accordance with a $1^{st}$ independent aspect, a fluid warming device for an extracorporeal blood treatment apparatus, comprises:
a casing delimiting a heating zone accommodating or configured to accommodate a fluid warming path, wherein the fluid warming path has an inlet and an outlet connected or connectable to an extracorporeal blood treatment apparatus;
heating elements operatively active in the heating zone to heat the fluid warming path;
at least a site temperature sensor operatively active on a site along the fluid warming path to detect a measured temperature of a fluid in the fluid warming device; wherein optionally said at least a site temperature sensor is an outlet temperature sensor operatively active at the outlet of the fluid warming path to detect a measured outlet temperature of a fluid leaving the fluid warming device;
an electronic control unit operatively connected at least to the site temperature sensor;
wherein the electronic control unit is configured to perform at least the following procedure:
receiving, from the site temperature sensor a signal correlated to the measured site temperature;
correcting the measured site temperature through a correction model to obtain an actual fluid site temperature;
wherein the correction model is a mathematical model of a measurement error, the measurement error being a difference between the measured site temperature and the actual fluid site temperature.

In particular, the correction model is an empirical model of a measurement error derived from a plurality of experimental data sets.

Optionally, the site temperature sensor is an inlet temperature sensor or an outlet temperature sensor or a temperature sensor placed between the inlet and the outlet.

Optionally, the electronic control unit is configured to adjust a heating power of the heating elements to keep the actual fluid site temperature at a set reference temperature value.

Optionally, the electronic control unit is configured to adjust a heating power of the heating elements to keep the actual fluid outlet temperature at a set reference temperature value.

Optionally, the site temperature sensor is other than the outlet temperature sensor and the electronic control unit is configured to perform the following procedure:
deriving an actual fluid outlet temperature from the actual fluid site temperature;
adjusting a heating power of the heating elements to keep the actual fluid outlet temperature at a set reference temperature value.

In accordance with a $2^{nd}$ independent aspect, an extracorporeal blood treatment apparatus, comprises:
a blood treatment device;
an extracorporeal blood circuit coupled to the blood treatment device;
a blood pump, a pump section of the extracorporeal blood circuit being configured to be coupled to the blood pump;
optionally, a treatment fluid circuit operatively connected to the extracorporeal blood circuit and/or to the blood treatment device;
at least a fluid warming device coupled or configured to be coupled to the extracorporeal blood circuit to heat blood and/or to the treatment fluid circuit to heat treatment fluid/s;
wherein the fluid warming device is according to the $1^{st}$ aspect and/or includes one or more of the following aspects.

In accordance with a $3^{rd}$ independent aspect, a method for detecting a fluid temperature at a site of a fluid warming device for an extracorporeal blood treatment apparatus, optionally at an outlet of a fluid warming device for an extracorporeal blood treatment apparatus is disclosed,
wherein the fluid warming device comprises:
a casing delimiting a heating zone accommodating or configured to accommodate a fluid warming path, wherein the fluid warming path has an inlet and an outlet connected or connectable to an extracorporeal blood treatment apparatus;
heating elements operatively active in the heating zone to heat the fluid warming path;
at least a site temperature sensor operatively active on a site along the fluid warming path to detect a measured temperature of a fluid in the fluid warming device; wherein optionally said at least a site temperature sensor is an outlet temperature sensor operatively active at the outlet of the fluid warming path to detect a measured outlet temperature of a fluid leaving the fluid warming device;
wherein the method, optionally performed by a control unit of the fluid warming device, comprises:
building a correction model function of a measurement error or a correction model as a mathematical model of a measurement error, in particular a correction model as an empirical model of a measurement error derived from a plurality of experimental data sets, the measurement error being a difference between the measured site temperature and an actual fluid site temperature;
correcting the measured site temperature through the correction model to obtain the actual fluid site temperature.

In a $4^{th}$ aspect according to the $1^{st}$ or $2^{nd}$ or $3^{rd}$ aspect, the fluid warming device is a blood warming device and is coupled or configured to be coupled to the extracorporeal blood circuit to heat blood, optionally to a blood return line of the extracorporeal blood circuit.

In a 5$^{th}$ aspect according to the 1$^{st}$, 2$^{nd}$ or 3$^{rd}$ aspect, the fluid warming device is a treatment fluid warming device and is coupled or configured to be coupled to the treatment fluid circuit to heat treatment fluid/s. Optionally, the blood treatment device comprises a blood chamber and a fluid chamber separated from one another by a semipermeable membrane. Optionally, the treatment fluid circuit comprises the fluid chamber, a dialysis line connected to the fluid chamber and, optionally, a fluid evacuation line connected to the fluid chamber. Optionally, the treatment fluid circuit comprises an infusion circuit comprising one or more infusion lines of a replacement fluid.

In a 6$^{th}$ aspect according to any of the previous aspects, the correction model is derived from a regression analysis of the measurement error, in particular collected through said plurality of experimental data sets, versus a plurality of parameters; the plurality of parameters being optionally collected through said plurality of experimental data sets.

In a 7$^{th}$ aspect according to the previous aspect, said parameters comprise the measured site temperature, optionally measured outlet temperature, and at least one further working parameter of the fluid warming device.

In an 8$^{th}$ aspect according to aspect 6 or 7, said parameters comprise the measured site temperature, optionally measured outlet temperature, and at least one further working parameter of the extracorporeal blood treatment apparatus.

In a 9$^{th}$ aspect according to the previous aspect, the at least one further working parameter is a temperature of a heating element of the fluid warming device.

In a 10$^{th}$ aspect according to the previous aspect 8 or 9, the at least one further working parameter is a heating power of the fluid warming device.

In an 11$^{th}$ aspect according to any of the previous aspects 8 to 10, the at least one further working parameter is a measured inlet temperature of the fluid entering the fluid warming device.

In a 12$^{th}$ aspect according to the previous aspect 8 to 11, the at least one further working parameter is at least one measured compensation temperature, wherein optionally the compensation temperature may be a temperature of a part of the fluid warming device and/or an ambient temperature. Optionally, the compensation ambient temperature may originate from an operator input or may be measured through another device of the blood treatment apparatus or of another independent device.

In a 13$^{th}$ aspect according to any of the previous aspects 8 to 12, the at least one further working parameter is a fluid flow rate.

In a 14$^{th}$ aspect according to any of previous aspects 8 to 13, the at least one further working parameter is a ratio between a heating power of the fluid warming device and a difference between the measured outlet temperature and a measured inlet temperature.

Optionally, the at least one further working parameter is a power supply voltage of the fluid warming device.

In a 15$^{th}$ aspect according to any of the previous aspects, the plurality of experimental data sets substantially covers a full intended operating range of the fluid warming device. Optionally, the plurality of experimental data sets are retrieved through a plurality of different bags or cassettes and/or of different control units.

In a 16$^{th}$ aspect according to the previous aspect, the full intended operating range is defined by at least one of the following ranges:

operating range of the actual fluid site temperature;
operating range of the measured site temperature;
operating range of a fluid flow rate;
operating range of a temperature of heating element/s;
operating range of a heating power;
operating range of an actual or measured inlet temperature;
operating range of at least one measured compensation temperature;
operating range of ambient temperature;
operating range of power supply voltage.

In a 17$^{th}$ aspect according to any of the previous aspects, a number of the experimental data sets is greater than thirty, optionally greater than fifty.

In an 18$^{th}$ aspect according to any of the previous aspects, the fluid warming device comprises an inlet temperature sensor operatively active at the inlet of the fluid warming path to detect a measured inlet temperature of the fluid entering the fluid warming device.

In a 19$^{th}$ aspect according to the previous aspect, the electronic control unit is configured to perform at least the following procedure: receiving from the inlet temperature sensor a signal correlated to the measured inlet temperature.

In a 20$^{th}$ aspect according to any of the previous aspects, the fluid warming device comprises at least a heating element temperature sensor coupled to a heating element or elements of the fluid warming device to detect a measured temperature of the heating element or elements.

In a 21$^{st}$ aspect according to the previous aspect, the electronic control unit is configured to perform at least the following procedure: receiving from the heating element temperature sensor a signal correlated to the measured temperature of the heating element.

In a 22$^{nd}$ aspect according to any of the previous aspects, the fluid warming device comprises at least one compensation temperature sensor located between the site temperature sensor and a heating element or elements to detect a measured temperature of a part of the fluid warming device.

In a 23$^{rd}$ aspect according to the previous aspect, the electronic control unit is configured to perform at least the following procedure: receiving from the compensation temperature sensor a signal correlated to the measured temperature of the part of the fluid warming device.

In a 24$^{th}$ aspect according to any of the previous aspects, the electronic control unit is configured to perform at least the following procedure: receiving a signal correlated to a heating power of the fluid warming device.

In a 25$^{th}$ aspect according to any of the previous aspects, the electronic control unit is configured to perform at least the following procedure: receiving a signal correlated to a fluid flow rate.

In a 26$^{th}$ aspect according to at least one of the previous aspects 19, 21, 23, 24, 25, the electronic control unit is configured to perform at least the following procedure: calculating the actual fluid site temperature from the measured site temperature and from at least one of: the measured inlet temperature, the measured temperature of the heating element, the measured temperature of the part of the fluid warming device, the heating power, the fluid flow rate.

In a 27$^{th}$ aspect according to the previous aspect, calculating is performed through the correction model.

In a 28$^{th}$ aspect according to any of the previous aspects, the site temperature sensor is contact type.

In a 29$^{th}$ aspect according to the previous aspect, the site temperature sensor is a thermistor or a thermocouple.

In a 30th aspect according to any of previous aspects 28 or 29, the contact type site temperature sensor is in contact or it is configured to be placed in contact with a site of the fluid warming path.

In a 31st aspect according to the previous aspect, the fluid warming path comprises channel/s and/or chamber/s delimited by walls.

In a 32nd aspect according to the previous aspect, the walls are of soft or stiff material.

In a 33rd aspect according to the previous aspects 31 or 32, a material of the walls is plastic.

In a 34th aspect according to the previous aspects 31 or 32 or 33, the contact type site temperature sensor is in contact or it is configured to be placed in contact with at least one of said walls.

In a 35th aspect according the any of the previous aspects, the fluid warming path comprises a bag, optionally soft, or a cassette, the fluid warming bag or cassette delimiting the fluid warming path and presenting the inlet and the outlet.

In a 36th aspect according to any of the previous aspect, the bag comprises two sheets of plastic (e.g. polyurethane or polyvinylchloride) superposed and welded to delimit inside the bag said fluid warming path.

In a 37th aspect according to previous aspects 35 or 36, the casing delimits a heating seat configured to accommodate the bag or cassette.

In a 38th aspect according to the previous aspect, the heating elements comprise at least one heating plate, optionally two opposite heating plates delimiting the heating seat, to heat the fluid warming bag or cassette.

In a 39th aspect according to any of previous aspects 35 to 38, the outlet temperature sensor is mounted in the casing and it is in contact or it is configured to be placed in contact with the outlet of the fluid warming bag or cassette.

In a 40th aspect according to any of previous aspects 35 to 39, an inlet temperature sensor is mounted in the casing and it is in contact or it is configured to be placed in contact with the inlet of the fluid warming bag or cassette.

The wording "in contact" through description and claims means that the contact type site/outlet/inlet temperature sensor rests against the site/outlet/inlet of the fluid warming path or rests against a heat conducting element, like a metal platelet, and the heat conducting element rests against the site/outlet/inlet of the fluid warming path. In both cases the contact type site/outlet/inlet temperature sensor measures its own temperature once reached the thermal equilibrium with the fluid warming path.

In a 41st aspect according to previous aspect 38, a heating plate temperature sensor, optionally a plurality of heating plate temperature sensors, is/are coupled to the heating plate or plates.

In a 42nd aspect according to the previous aspect, the heating plate temperature sensors are located along the fluid warming path.

In a 43rd aspect according to the previous aspects 22 or 23, the at least one compensation temperature sensor comprises a compensation temperature sensor to sense the temperature of the casing.

In a 44th aspect according to the previous aspects 22 or 23, the at least one compensation temperature sensor comprises a compensation temperature sensor placed at or close to a location of a printed circuit board assembly operatively connected to the outlet temperature sensor.

In a 45th aspect according to any of the previous aspects, the casing comprises a holder, optionally a plastic holder, for the outlet temperature sensor.

In a 46th aspect according to the previous aspect when according to aspect 22 or 23, the at least one compensation temperature sensor comprises a holder compensation temperature sensor coupled to the holder of the outlet temperature sensor.

In accordance with a 47th independent aspect, a method for controlling a fluid warming device for an extracorporeal blood treatment apparatus comprises the method for detecting a fluid temperature at a site of the fluid warming device of the 3rd aspect and further comprises:

adjusting a heating power of the heating elements to keep the actual fluid site temperature at a set reference temperature value.

In a 48th aspect according to any of the previous aspects, the heating zone comprises a plurality of subzones configured to be heated independently.

In a 49th aspect according to the previous aspect, each subzone comprises respective heating element or elements.

In a 50th aspect according to the previous aspect, the heating zone comprises at least a first subzone at the inlet of the fluid warming bag or cassette and a second subzone at the outlet of the fluid warming bag or cassette.

In a 51st aspect according to the previous aspect, if the site temperature is the outlet temperature, the at least one further working parameter is a heating power of the second subzone of the fluid warming device. In the multi zone design, power used in the last heating zone allows for better correction than the total power.

In a 52nd aspect according to aspect 50, if the site temperature is the inlet temperature, the at least one further working parameter is a heating power of the first subzone of the fluid warming device.

DESCRIPTION OF DRAWINGS

The following drawings relating to aspects of the invention are provided by way of non-limiting example.

DETAILED DESCRIPTION

Figure 1:
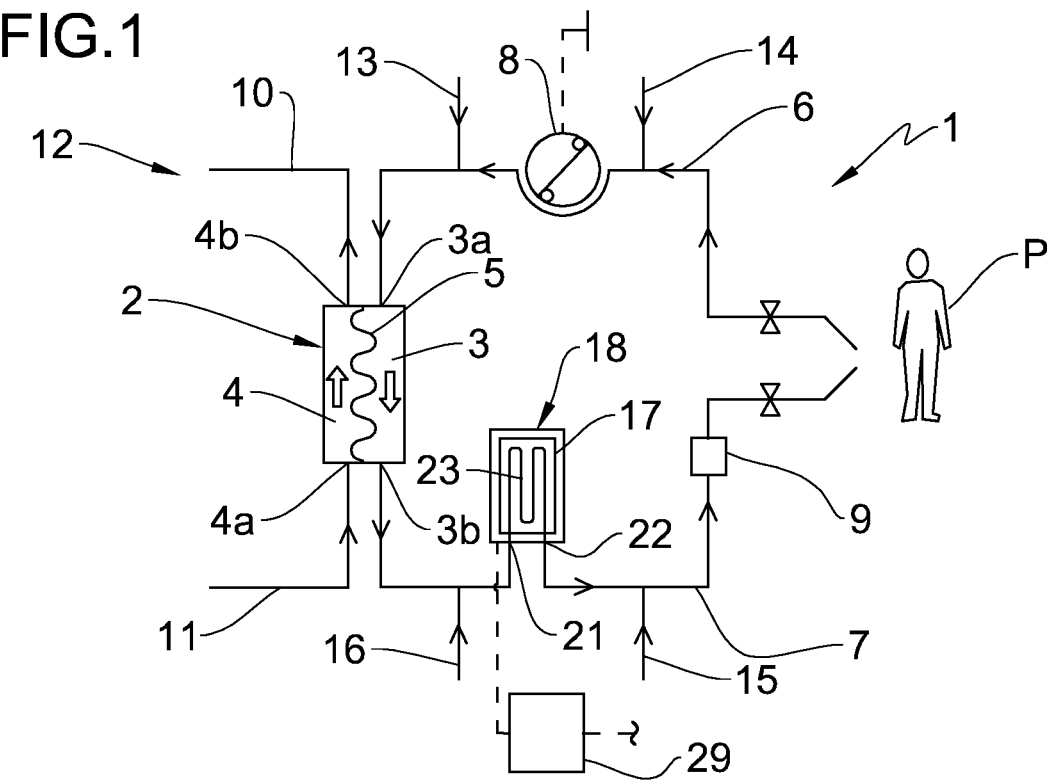
FIG. 1 shows a schematic representation of an extracorporeal blood treatment apparatus provided with a fluid warming device according to the present invention.

With reference to the appended drawings, FIG. 1 shows a schematic representation of an extracorporeal blood treatment apparatus 1. The apparatus 1 comprises one blood treatment device 2, for example a hemofilter, a hemodiafilter, a plasmafilter, a dialysis filter, an absorber or other unit suitable for processing the blood taken from a patient P.

The blood treatment device 2 has a first compartment or blood chamber 3 and a second compartment or fluid chamber 4 separated from one another by a semipermeable membrane 5. A blood withdrawal line 6 is connected to an inlet port 3a of the blood chamber 3 and is configured, in an operative condition of connection to the patient P, to remove blood from a vascular access device inserted, for example in a fistula on the patient P. A blood return line 7 connected to an outlet port 3b of the blood chamber 3 is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on. The blood withdrawal line 6 and the blood return line 7 are part of an extracorporeal blood circuit of the apparatus 1.

The extracorporeal blood circuit 6, 7 and the treatment unit 2 are usually disposable parts which are loaded onto a frame of a blood treatment machine, not shown.

As shown in FIG. 1, the apparatus 1 comprises at least a first actuator, in the present example a blood pump 8, which is part of said machine and operates at the blood withdrawal line 6, to cause movement of the blood removed from the patient P from a first end of the withdrawal line 6 connected to the patient P to the blood chamber 3. The blood pump 8 is, for example, a peristaltic pump, as shown in FIG. 1, which acts on a respective pump section of the withdrawal line 6.

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 6 connected to the patient P towards the blood chamber 3 and then from the blood chamber 3 towards a second end of the blood return line 7 connected to the vascular access of the patient P.

The apparatus 1 may further comprise an air trapping device 9 operating on the blood return line 7 (the air trapping device 9 may be a venous deaeration chamber). The air trapping device 9 is placed online in the blood return line 7.

A first section of the blood return line 7 puts in fluid communication the outlet port 3b of the blood chamber 3 with the air trapping device 9 and a second section of the blood return line 7 puts in fluid communication the air trapping device 9 with the patient P. The blood coming from the blood chamber 3 of the treatment device 2 enters and exits the air trapping device 9 before reaching the patient P.

The apparatus 1 of FIG. 1 further comprises one fluid evacuation line 10 connected with an outlet port 4b of the fluid chamber 4 such as to receive the filtered waste fluid through the semipermeable membrane 5. The fluid evacuation line 10 receives such filtered waste fluid coming from the fluid chamber 4 of the treatment device 2, for example, comprising used dialysis liquid and/or liquid ultra-filtered through the membrane 5. The fluid evacuation line 10 leads to a receiving element, not shown, for example having a collection bag or a drainage pipe for the waste fluid. One or more dialysate pumps, not shown, may operate on the fluid evacuation line 10.

In the example of FIG. 1, a dialysis line 11 is also present for supplying a fresh treatment fluid into the inlet port 4a of the fluid chamber 4. The presence of this dialysis line 11 is not strictly necessary since, in the absence of the dialysis line 11, the apparatus 1 is still able to perform treatments such as ultrafiltration, hemofiltration or plasma-filtration. In case the dialysis line 11 is present, a fluid flow intercept device may be used, not shown, to selectively allow or inhibit fluid passage through the dialysis line 11, depending on whether or not a purification by diffusive effect is to be performed inside the treatment device 2.

The dialysis line 11, if present, is typically equipped with a dialysis pump and is able to receive a fresh fluid from a module, not shown, for example a bag or on-line preparation section of dialysis fluid, and to send such a fluid to the inlet port 4a of the fluid chamber 4.

The fluid evacuation line 10, the dialysis line 11 and the fluid chamber 4 are part of a treatment fluid circuit 12.

The apparatus 1 as shown in FIG. 1 further comprises an infusion circuit comprising one or more infusion lines of a replacement fluid. According to the embodiment of FIG. 1, a pre-infusion line 13 is connected to the blood withdrawal line 6 between the blood pump 8 and the inlet port 3a of the blood chamber 3. A pre pump infusion line 14 is connected to the blood withdrawal line 6 upstream of the blood pump 8, between said blood pump 8 and the vascular access device inserted in the fistula on the patient P. A post-infusion line 15, 16 is connected to the blood return line 7 for performing HF or HDF treatments. Usually one or two post-infusion lines are used connected upstream of or to the air trapping device 9. FIG. 1 shows that the post-infusion line comprises a first and a second branch 15, 16. Each of the pre- and/or post-infusion line 13, 14, 15, 16 is provided with a respective pump, not shown. The pre- and/or post-infusion lines 13, 14, 15, 16 may be supplied by fluid coming from bags or directly by infusion fluid prepared on-line. Each of the pre- and/or post-infusion lines 13, 14, 15, 16 are part of the treatment fluid circuit 12. The specific configuration of the pre- and post-infusion circuits may of course differ from those shown in FIG. 1.

The blood return line 7 presents a heating zone, for example interposed between the first and second branches 15, 16 of the post-infusion line. In said heating zone blood is warmed before flowing into the blood circulation system of the patient P. In the embodiment shown in the attached figures, the heated portion is part of a disposable blood warming bag 17 which is inserted into a blood warming device 18. The blood warming device 18 is connected to or is part of the extracorporeal blood treatment apparatus 1.

Figure 2:
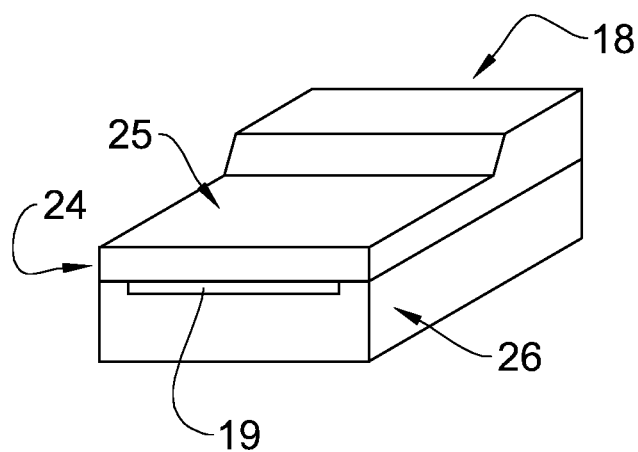
FIG. 2 shows a schematic perspective view of the fluid warming device of FIG. 1.
Figure 3:
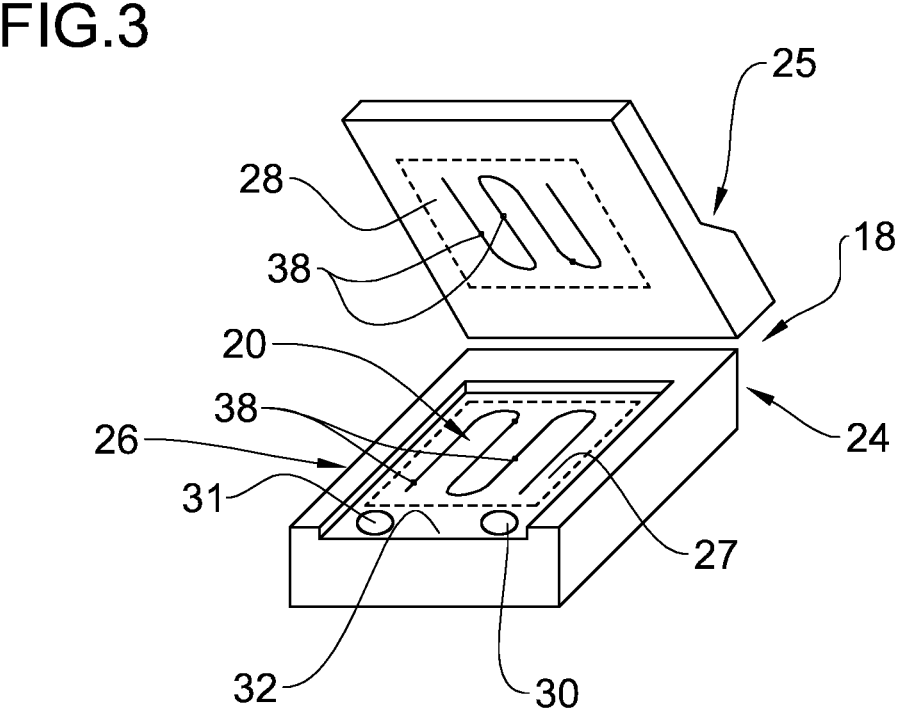
FIG. 3 shows the fluid warming device of FIG. 1 in an open configuration.
Figure 4:
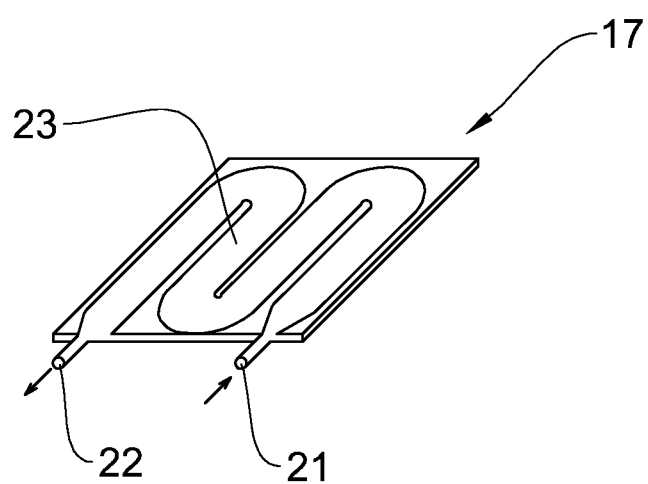
FIG. 4 is a disposable fluid warming bag to be used with the fluid warming device of FIGS. 2 and 3.

The blood warming bag 17 shown in the attached figures is a substantially flat and soft bag insertable through a slot 19 in a heating seat 20 provided in the blood warming device 18 (FIGS. 2 and 3).

The blood warming bag 17 presents an inlet 21 and an outlet 22 connected to the extracorporeal blood circuit. For instance, the blood warming bag 17 comprises two sheets of plastic (e.g. polyurethane or polyvinylchloride) superposed and welded to form the bag and to form, inside the bag, a fluid warming path 23 delimited by said two sheets and by lines of welding.

The inlet 21 and the outlet 22 are tube sections placed at opposite ends of the fluid warming path 23. These tube sections of the inlet 21 and the outlet 22 protrude from a side of the blood warming bag 17 and are substantially parallel to each other.

The blood warming device 18 comprises a casing 24 delimiting the heating seat 20 configured to accommodate the blood warming bag 17. The casing 24 comprises an upper part 25 and a lower part 26 which may be linked and movable between a working configuration (shown in FIG. 2) and a maintenance configuration (shown in FIG. 3). The upper part 25 and lower part 26 of FIGS. 2 and 3 are hinged to move between the mentioned configurations. When the casing 24 is in the working configuration of FIG. 2, the upper part 25 and the lower part 26 are juxtaposed and delimit inside the casing 24 the heating seat 20 which opens outside through the slot 19.

When the blood warming bag 17 is inserted in the seat through the slot 19, the inlet 21 and the outlet 22 of the blood warming bag 17 are disposed close to the slot 19 or protrude from said slot 19 to allow tubing of blood withdrawal line 6 and blood return line 7 to be connected to the other elements of the extracorporeal blood treatment apparatus 1.

An upper face of the lower part 26 has a hollow delimiting a lower part of the heating seat 20 and shaped to accommodate the blood warming bag 17. The hollow presents a first heating plate 27 heated by a first heating device, not shown, placed underneath said first heating plate 27.

A lower face of the upper part 25 has a second heating plate 28 heated by a second heating device, not shown, placed underneath said second heating plate 28. The second heating plate 28 delimits an upper part of the heating seat 20. The first heating plate 27 and the second heating plate 28 are opposite and parallel surfaces delimiting the heating seat 20.

The first and second heating plates 27, 28 define heating elements for the blood warming bag 17. The first and second heating devices may be or may be connected to electrical resistors powered by a power control unit and controlled by an electronic control unit 29 in order to heat the blood warming path 23 in the blood warming bag 17.

In an embodiment, not shown, the heating zone comprises a plurality of subzones configured to be heated independently. By way of example, each of the first and second heating plates 27, 28 is divided into a plurality of parts each heated independently form the other part/s.

The blood warming device 18 comprises an inlet temperature sensor 30 and an outlet temperature sensor 31 embedded in a bottom surface 32 of the casing 24 close to the slot 19 (FIG. 3). The inlet temperature sensor 30 is operatively active at the inlet 21 of the blood warming path 23 to detect a measured inlet temperature of blood entering the blood warming device 18. The outlet temperature sensor 31 is operatively active at the outlet 22 of the blood warming path 23 to detect a measured outlet temperature of blood leaving the blood warming device 18.

Figure 5:
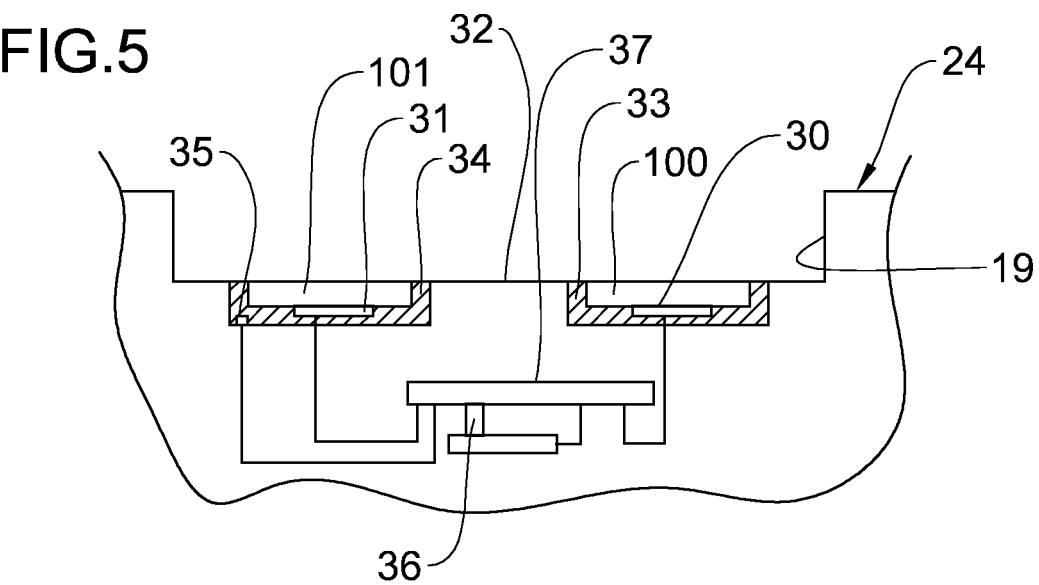
FIG. 5 shows a sectioned and enlarged view of a portion of the fluid warming device of FIG. 3.

The inlet temperature sensor 30 is a contact type temperature sensor, e.g. a temperature sensor integrated circuit (IC) with a thermistor or a thermocouple, housed in a plastic holder 33 (FIG. 5). The plastic holder 33 and the inlet temperature sensor 30 are housed in a seat fashioned in the bottom surface 32 of the casing 24. A heat conducting element, like an aluminum platelet 100, is mounted in the plastic holder 33. The aluminum platelet 100 opens on the bottom surface 32 and it is flush with said bottom surface 32. The inlet temperature sensor 30 is placed inside the plastic holder 33 and rests against the aluminum platelet 100 (FIG. 5).

Figure 6:
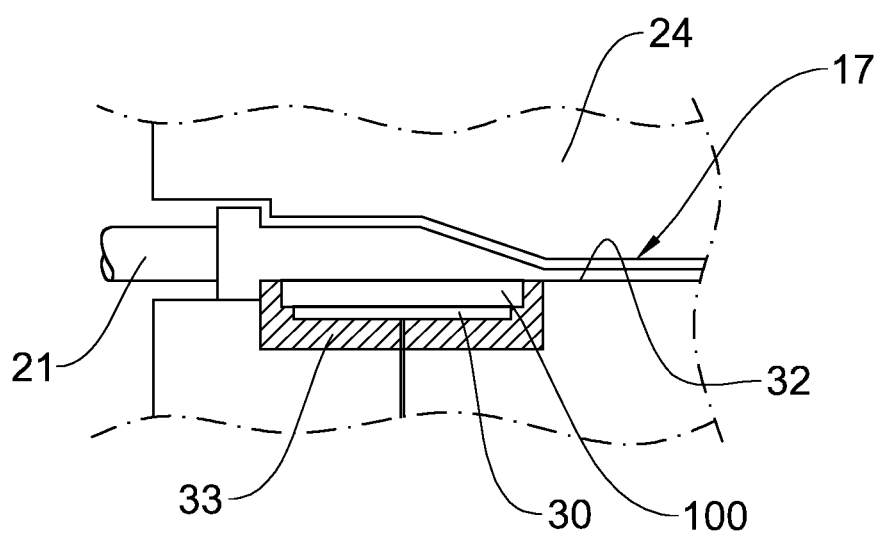
FIG. 6 shows a sectioned and enlarged view of another portion of the fluid warming device of FIG. 3.

When the blood warming bag 17 is correctly inserted in the seat, the inlet 21 of the blood warming bag 17 is in contact with the aluminum platelet 100 (FIG. 6). The inlet temperature sensor 30 detects the temperature Ti of the aluminum platelet 100 and of the inlet 21 through which the blood flows.

The outlet temperature sensor 31 is a contact type temperature sensor, e.g. a temperature sensor integrated circuit (IC) with a thermistor or a thermocouple, housed in a plastic holder 34 (FIG. 5). The plastic holder 34 and the outlet temperature sensor 31 are housed in a seat fashioned in the bottom surface 32 of the casing 24. The outlet temperature sensor 31 rests against a respective aluminum platelet 101 which opens on the bottom surface 32 and it is flush with said bottom surface 32 (FIG. 5).

When the blood warming bag 17 is correctly inserted in the seat, the outlet 22 of the blood warming bag 17 is in contact with the aluminum platelet 101. The outlet temperature sensor 31 detects the temperature of the aluminum platelet 101 and of the outlet 22 through which the warmed blood flows.

A holder compensation temperature sensor 35, e.g. a thermistor, is embedded in the plastic holder 34 of the outlet temperature sensor 31 to measure the temperature Tcomp1 of said plastic holder 34.

The blood warming device 18 comprises a further compensation temperature sensor 36, e.g. a temperature sensor integrated circuit (IC) with a thermistor or a thermocouple, placed in the casing 24 to sense the temperature of the casing 24.

Ambient temperature Ta may also be used as compensation temperature. The ambient temperature Ta may be measured through a respective sensor of the extracorporeal blood treatment apparatus 1 or through an independent device and entered manually by an operator in the control unit 29.

A printed circuit board assembly (PCBA) 37 is mounted inside the casing 24 and, together with other printed circuit board assemblies, forms part of the electronic control unit 29 of the blood warming device 18.

In the illustrated embodiment, the further compensation temperature sensor 36, e.g. a thermocouple, is placed at or close to a location of the printed circuit board assembly 37 to sense the temperature Tcomp2 of said printed circuit board assembly 37.

The blood warming device 18 comprises a plurality of heating plate temperature sensors 38 coupled to the first and second heating plates 27, 28 to detect a measured temperature of the heating plates 27, 28. In the illustrated embodiment, each of the first and second heating plates 27, 28 is provided with three heating plate temperature sensors 38 which, when the blood warming bag 17 is accommodated inside the heating seat 20, are placed along the fluid warming path 23.

The temperature sensors (inlet temperature sensor 30, outlet temperature sensor 31, compensation temperature sensor 35, further compensation temperature sensor 36, heating plate temperature sensors 38) are operatively connected to the printed circuit board assembly 37 and to the electronic control unit 29.

The electronic control unit 29 may be part of the blood warming device 18 and connected to an electronic control unit of the apparatus 1 or may be the electronic control unit of the apparatus 1 itself.

The electronic control unit 29 may comprise a digital processor (CPU) and memory (or memories), an analog circuit, or a combination thereof, and input/output interfaces. Said control unit 29 may be the control unit which is configured to control the apparatus 1 during patient blood treatment through a software stored in the control unit 29. In the embodiment of FIG. 1, the electronic control unit 29 is connected at least to the blood pump 8 and to the power control unit, not shown, of the blood warming device 18.

The electronic control unit 29 is configured to control the actual fluid temperature Tout of treated blood leaving the blood warming device 18 and flowing back into the patient P through a heat controller algorithm. To this aim, the electronic control unit 29 receives the measured outlet temperature To from the outlet temperature sensor 31, performs a correction of the measured outlet temperature To according to the steps disclosed in the following (to improve accuracy of the measurement and to obtain a value very close to an actual blood outlet temperature Tout) and adjusts the heating power Ph of the power control unit to keep the actual outlet temperature Tout at a set reference temperature value Tset (set point). The electronic control unit 29 uses a closed-loop control to maintain desirable temperature at its outlet.

In order to correct the measured outlet temperature To, a correction mathematical model or algorithm is previously developed and stored in a memory of the electronic control unit 29 or connected to the electronic control unit 29. The correction mathematical model or algorithm may be embedded in the heat controller algorithm.

The correction model is an empirical model of a measurement error E derived from a plurality of experimental data sets gathered during development testing. The measurement error E is a difference between the measured outlet temperature To and the actual outlet temperature Tout.

The empirical correction model is built by carrying out a plurality of test treatments k. An experimental data set is collected for each test treatment k. Each experimental data set comprises a plurality of measured parameters, wherein said parameters comprise the measured outlet temperature $To_k$ and at least one further working parameter of the blood warming device 18 and/or of the extracorporeal blood treatment apparatus 1 for that test treatment k.

The measured parameters for each test treatment k may the following:

$To_k$ measured outlet temperature (through the outlet temperature sensor 31);
$Ti_k$ measured inlet temperature (through the inlet temperature sensor 32);
$Tplate_k$ measured heating plate/s temperature/s (through the heating plate temperature sensor/s 38);
$Ph_k$ heating power of the fluid warming device (through a signal from the power control unit);
$Tcomp1_k$ measured compensation temperature (through the compensation temperature sensor 35);
$Tcomp2_k$ measured further compensation temperature (through the further compensation temperature sensor 36);
$Q_k$ blood flow rate (through a signal from the blood pump 8 or communicated from a system controlling the blood flow);
$Tout_k$ measured actual fluid outlet temperature (measured during test treatments through an independent and very accurate sensor);
$Tin_k$ measured actual fluid inlet temperature (measured during test treatments through an independent and a very accurate non-contact sensor);
$Ta_k$ ambient temperature;
$Pw_k$ power supply voltage of the fluid warming device.

The blood flow rate Q may be replaced by a ratio Ph/(To−Ti) between the heating power Ph and a difference between the measured outlet temperature To and the measured inlet temperature Ti. Indeed, heating power transferred to the blood may be expressed by $Ph = \rho \times Cp \times Q \times (Tout-Tin)$ where Tin is the actual fluid inlet temperature. This relationship indicates that Ph/(To−Ti) should be proportional to the actual fluid flow rate.

Measured compensation temperature and measured further compensation temperature Tcomp1, Tcomp2 may be used in combination with measured heating plate/s temperature/s Tplate or in lieu of measured heating plate/s temperature/s Tplate.

The correction model may be derived from a regression analysis of the measurement error $E_k$ collected through said plurality of experimental data sets versus the mentioned parameters collected through said plurality of experimental data sets. The model will be as reliable as the experimental data set collection is large and covers the full intended operating range of the blood warming device 18 and it is built using several fluid warming devices 18 and several warmer bags/cassettes 17.

A number of the experimental data sets k may be thirty or more. The full intended operating range may be defined by ranges of the above mentioned parameters (ΔTo, ΔTi, ΔTplate, ΔPh, ΔTcomp1, ΔTcomp2, ΔQ, ΔTout, ΔTa, ΔPw). Several general regression models may be used according to the operating range/s of the blood warming device 18.

The empirical model may include: 1st and 2nd order terms of each of the parameters and/or crossed terms and/or other combinations of terms.

Once the empirical correction model is ready and stored in the memory of the electronic control unit 29, the electronic control unit 29 is configured to perform the following procedure during an extracorporeal blood treatment session performed on a patient P through the apparatus 1: receiving, from the outlet temperature sensor 31 a signal correlated to the measured outlet temperature To and correcting the measured outlet temperature To through the correction model to obtain the actual fluid outlet temperature Tout.

In addition to the measured outlet temperature To, the electronic control unit 29 receives as input at least one of the following measured parameters:

To measured outlet temperature (through the outlet temperature sensor 31);
Ti measured inlet temperature (through the inlet temperature sensor 32);
Tplate measured heating plate/s temperature/s (through the heating plate temperature sensor/s 38);
Ph heating power of the fluid warming device (through a signal from the power control unit);
Tcomp1 measured compensation temperature (through the compensation temperature sensor 35);
Tcomp2 measured further compensation temperature (through the further compensation temperature sensor 36);
Q blood flow rate (through a signal from the blood pump 8 or communicated from a system controlling the blood flow);
Ta ambient temperature;
Pw Power supply voltage.

Therefore, the actual fluid outlet temperature Tout is calculated from the measured outlet temperature and from at least one of To, Ti, Tplate, Ph, Tcomp1, Tcomp2, Q, Ta, Pw and through the corrective model/algorithm, which works as a transfer function.

Example of Empirical Modeling

An empirical model/algorithm was developed based on empirical data gathered during developmental testing. The test setup was comprised of a simulated patient (warm water reservoir), an extracorporeal CRRT apparatus, and a blood warming device. The blood warming device outlet was instrumented with independent temperature sensors at the inlet and outlet in order to read the actual fluid temperatures at those points.

Outlet measurement error E was defined as the measured outlet temperature To minus the actual fluid temperature Tout at the outlet. In equation form: E=To−Tout.

Three metrics were used to compare against the outlet error E. Each metric was the difference between a specific secondary sensor and the measured outlet temperature.

In equation form:

$$DTcomp1 = To - Tcomp1$$

$$DTcomp2 = To - Tcomp2$$

$$DTplate = To - Tplate$$

where Tcomp1, Tcomp2 and Tplate were the measured temperatures at outlet temperature sensor 31, further compensation temperature sensor 36 and the heating plate temperature sensor 38 of the first heating plate 27 closest to the outlet temperature sensor 31, respectively.

Figure 7:
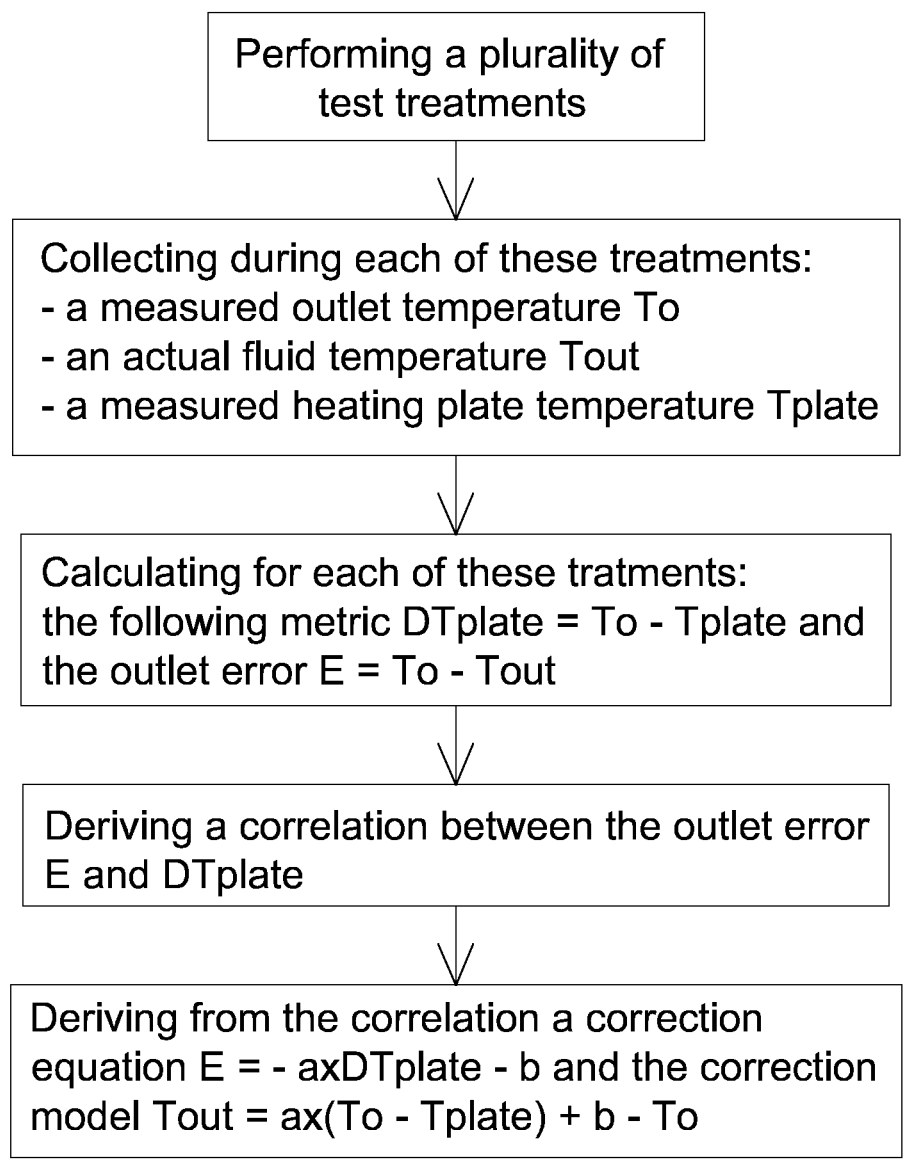
FIG. 7 is a flowchart showing steps for a building a correction model according to a method of the present invention.
Figure 8:
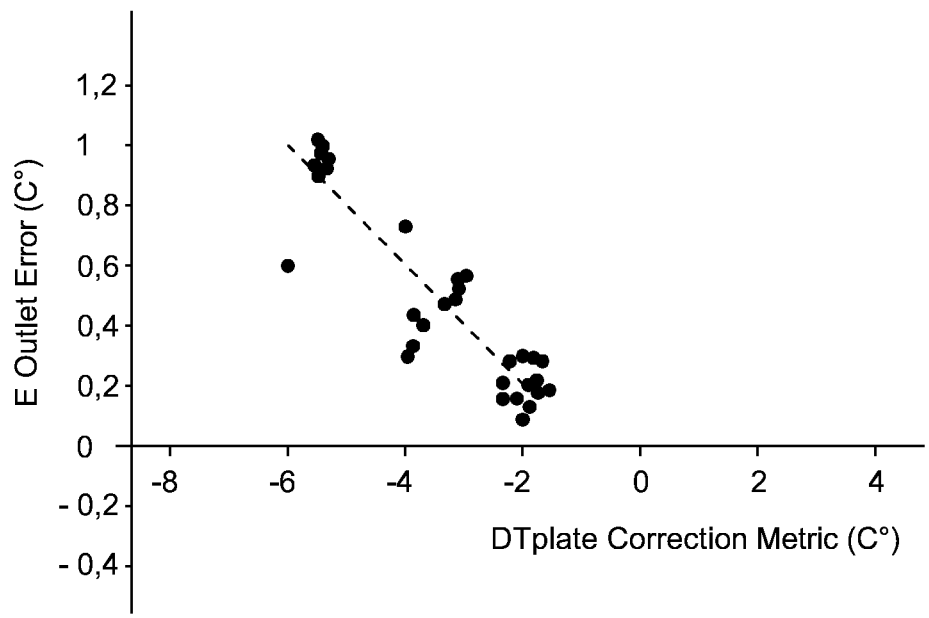
FIG. 8 shows a cumulative plot of results used to build the correction model.

To examine if there was a correlation between outlet error and any of these metrics, data was gathered from numerous test treatments. Treatments were performed using a hot water bath connected to a filter set on a blood treatment apparatus 1 with a blood warming device 18 attached. In order to calculate each metric once per treatment, the metrics were averaged over the time period at which the blood warming device 18 was at steady state. In other words, each treatment had a mean steady state outlet error DTcomp1, DTcomp2 and DTplate. A flow chart related to DTplate is shown in FIG. 7 and a cumulative plot of the results related to DTplate is shown in FIG. 8.

This plot shows a strong linear correlation between outlet error and DTplate. From this correlation, a correction equation may be derived:

$$E = -a \times DTplate - b$$

$$To - Tout = -a \times (To - Tplate) - b$$

$$Tout = a \times (To - Tplate) + b - To$$

where Tout is the estimated fluid temperature at the outlet.

Example of Closed Loop Correction

Figure 9:
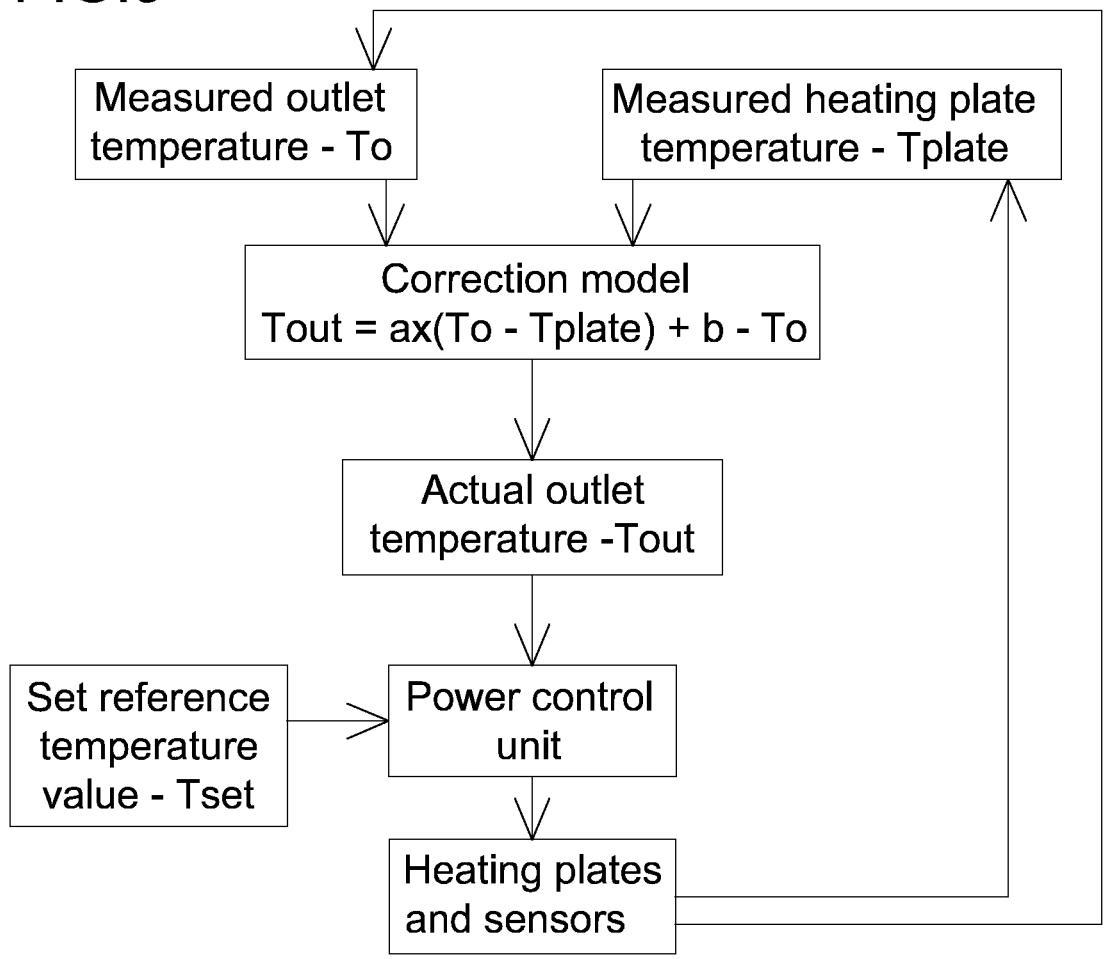
FIG. 9 is a flowchart showing a method for controlling the fluid warming device according to the present invention.

This equation was implemented in the electronic control unit 29 with the constants a and b shown in in the last block of FIG. 7. This implementation is illustrated in block diagram form in FIG. 9. As shown in this figure, the outlet correction is part of the feedback loop within the electronic control unit 29.

The warming device 18 according to the invention herewith disclosed may also be designed to be coupled or configured to be coupled to the treatment fluid circuit to heat treatment fluid/s.

In lieu of the blood warming device or in combination with said blood warming device, one or more treatment fluid warming device/s 18 may be coupled to one or more of the pre- and/or post-infusion lines 13, 14, 15, 16 or the dialysis line 11.

In these embodiments, blood is warmed by the treatment fluids.

The correction model above disclosed may be applied to temperature sensor or sensors other than the outlet temperature sensor, e.g. to a generic site of the flow path in the fluid warming device 18. The correction model may be applied to the measured inlet temperature to calculate the actual fluid inlet temperature Tin. Actual fluid inlet temperature Tin may be used to perform, e.g., internal consistency checks of the fluid warming device, malfunction, diagnostic, etc.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. Fluid warming device for an extracorporeal blood treatment apparatus, the fluid warming device comprising:
   a casing defining a heating zone configured to accommodate a fluid warming path, wherein the fluid warming path is defined by a fluid warming bag or a cassette comprising an inlet and an outlet configured for fluid connection to an extracorporeal blood treatment apparatus, wherein the casing delimits a heating seat configured to accommodate the fluid warming bag or the cassette;
   heating elements operatively active in the heating zone, the heating elements configured to heat the fluid warming path and comprising two opposite heating plates delimiting the heating seat to heat the fluid warming bag or cassette, the fluid warming device comprising a plurality of heating element temperature sensors coupled to the two opposite heating plates and located along the fluid warming path to detect a measured temperature of the two opposite heating plates;
   an outlet temperature sensor operatively active at the outlet of the fluid warming path and configured to convey a measured outlet temperature of a fluid leaving the fluid warming device;
   an inlet temperature sensor operatively active at the inlet of the fluid warming path and configured to detect a measured inlet temperature of the fluid entering the fluid warming device;
   a compensation temperature sensor located between the outlet temperature sensor and the heating element and configured to detect a measured temperature of a part of the fluid warming device; and
   an electronic control unit operatively connected to the outlet temperature sensor, the inlet temperature sensor, the plurality of heating element temperature sensors, the compensation temperature sensor, and the heating elements, wherein the electronic control unit is configured to:
   receive from the inlet temperature sensor a signal correlated to the measured inlet temperature;
   receive from one or more of the plurality of heating element temperature sensors a signal correlated to the measured temperature of one heating element of the plurality of heating elements;
   receive from the compensation temperature sensor a signal correlated to the measured temperature of the part of the fluid warming device;
   receive, from the outlet temperature sensor a signal correlated to the measured outlet temperature;
   correct the measured outlet temperature using a correction model to obtain an actual fluid outlet temperature and calculate an actual fluid outlet temperature from the measured outlet temperature and from at least one of: the measured inlet temperature, the measured temperature of the heating element, and the measured temperature of the part of the fluid warming device;
   adjust a heating power of the heating elements to keep the actual fluid outlet temperature at a set reference temperature;
   wherein the correction model is based at least in part on a measurement error, the measurement error being a difference between the measured outlet temperature and the actual fluid outlet temperature.

2. The fluid warming device of claim 1, wherein the fluid warming device is a blood warming device configured to be coupled to a blood return line of an extracorporeal blood circuit of the extracorporeal blood treatment apparatus to heat blood.

3. The fluid warming device of claim 1, wherein the outlet temperature sensor is a contact type outlet temperature sensor, wherein the contact type outlet temperature sensor is configured to be placed in contact with an outlet of the fluid warming path.

4. The fluid warming device of claim 1, wherein the casing comprises a holder housing the outlet temperature sensor, the holder and the outlet temperature sensor being housed in a seat of the casing, wherein a heat conducting element is mounted in the holder and the outlet temperature sensor rests against the heat conducting element and is configured to detect a temperature of the heat conducting element.

5. The fluid warming device of claim 4, wherein the heat conducting element opens on a bottom surface of the casing and is flush with said bottom surface, the heat conducting element being in contact with the outlet of the fluid warming path, the outlet temperature sensor configured to detect a temperature of the heat conducting element and indirectly of the outlet of the fluid warming path.

6. Fluid warming device for an extracorporeal blood treatment apparatus, the fluid warming device comprising:
a casing defining a heating zone configured to accommodate a fluid warming path, wherein the fluid warming path is defined by a fluid warming bag or a cassette comprising an inlet and an outlet configured for fluid connection to an extracorporeal blood treatment apparatus;
heating elements operatively active in the heating zone, the heating elements configured to heat the fluid warming path and comprising two opposite heating plates delimiting the heating seat to heat the fluid warming bag or cassette, the fluid warming device comprising a plurality of heating element temperature sensors coupled to the two opposite heating plates and located along the fluid warming path to detect a measured temperature of the two opposite heating plates;
an outlet temperature sensor operatively active at the outlet of the fluid warming path and configured to convey a measured outlet temperature of a fluid leaving the fluid warming device;
at least one heating element temperature sensor coupled to one of the heating elements of the fluid warming device and configured to detect a measured temperature of the heating element;
an electronic control unit operatively connected to the outlet temperature sensor, the heating elements, and the at least one heating element temperature sensor, wherein the electronic control unit is configured to:
receive, from the outlet temperature sensor, a signal correlated to the measured outlet temperature;
receive, from the at least one heating element temperature sensor, a signal correlated to the measured temperature of the heating element;
correct the measured outlet temperature using a correction model to obtain an actual fluid outlet temperature;
control the heating elements to keep the actual fluid outlet temperature at a set reference temperature;
wherein the electronic control unit is configured to obtain the actual fluid outlet temperature as a function of a difference between the measured outlet temperature and the measured temperature of the heating element.

7. The fluid warming device of claim 6, wherein the electronic control unit is configured to calculate the actual fluid outlet temperature as a linear function of the difference between the measured outlet temperature and the measured temperature of the heating element.

8. The fluid warming device of claim 6, wherein the electronic control unit is configured to calculate the actual fluid outlet temperature as follows:

$$T_{out} = a \cdot (T_O - T_{plate}) - T_O + b$$

wherein
$T_{out}$ is the actual fluid outlet temperature;
$T_O$ is the measured outlet temperature;
$T_{plate}$ is the measured temperature of the heating element; and
a, b are constants.

9. The fluid warming device of claim 6, comprising:
an inlet temperature sensor operatively active at the inlet of the fluid warming path and configured to detect a measured inlet temperature of the fluid entering the fluid warming device;
a compensation temperature sensor located between the outlet temperature sensor and the heating element and configured to detect a measured temperature of a part of the fluid warming device;
wherein the electronic control unit is operably connected to the inlet temperature sensor and the compensation temperature sensor, wherein the electronic control unit is further configured to:
receive from the inlet temperature sensor a signal correlated to the measured inlet temperature;
receive from the compensation temperature sensor a signal correlated to the measured temperature of the part of the fluid warming device;
calculate the actual fluid outlet temperature from the measured outlet temperature, the measured temperature of the heating element and from at least one of: the measured inlet temperature, and the measured temperature of the part of the fluid warming device.

10. The fluid warming device of claim 9, wherein the compensation temperature sensor is configured to sense the temperature of the casing at a location between the site temperature sensor and the heating elements to detect a measured temperature of the casing.

11. A fluid warming device for an extracorporeal blood treatment apparatus, the fluid warming device comprising:
a casing defining a heating zone configured to accommodate a fluid warming path, wherein the fluid warming path is defined by a fluid warming bag or a cassette comprising an inlet and an outlet configured for fluid connection to an extracorporeal blood treatment apparatus;
heating elements operatively active in the heating zone and configured to heat the fluid warming path and comprising two opposite heating plates delimiting the heating seat to heat the fluid warming bag or cassette, the fluid warming device comprising a plurality of heating element temperature sensors coupled to the two opposite heating plates and located along the fluid warming path to detect a measured temperature of the two opposite heating plates;
at least one site temperature sensor operatively active on a site along the fluid warming path to detect a measured site temperature of a fluid in the fluid warming device;

an electronic control unit operatively connected to the plurality of heating element temperature sensors, the at least one site temperature sensor, and the heating elements, wherein the electronic control unit is configured to:

receive, from the at least one site temperature sensor, a signal correlated to the measured site temperature;

receive from one or more of the plurality of heating element temperature sensors a signal correlated to the measured temperature of one of the heating elements:

correct the measured site temperature using a correction model to obtain an actual fluid site temperature and calculate the actual fluid site temperature from the measured site temperature and from the measured temperature of the heating element;

adjusting the heating elements based on the actual fluid site temperature to keep an actual fluid temperature in a further site along the fluid warming path at a set reference temperature value.

12. The fluid warming device of claim 11, wherein the at least one site temperature sensor is one among an inlet temperature sensor, an outlet temperature sensor, and a temperature sensor placed between the inlet and the outlet.

13. The fluid warming device of claim 11, wherein the at least one site temperature sensor is other than an outlet temperature sensor and the electronic control unit is configured to:

determine an actual fluid outlet temperature from the actual fluid site temperature;

adjust a heating power of the heating elements to keep the actual fluid outlet temperature at a set reference temperature value.

14. The fluid warming device of claim 11, wherein the correction model is based at least in part on a measurement error, the measurement error being a difference between the measured site temperature and the actual fluid site temperature.

* * * * *